Figure 1:
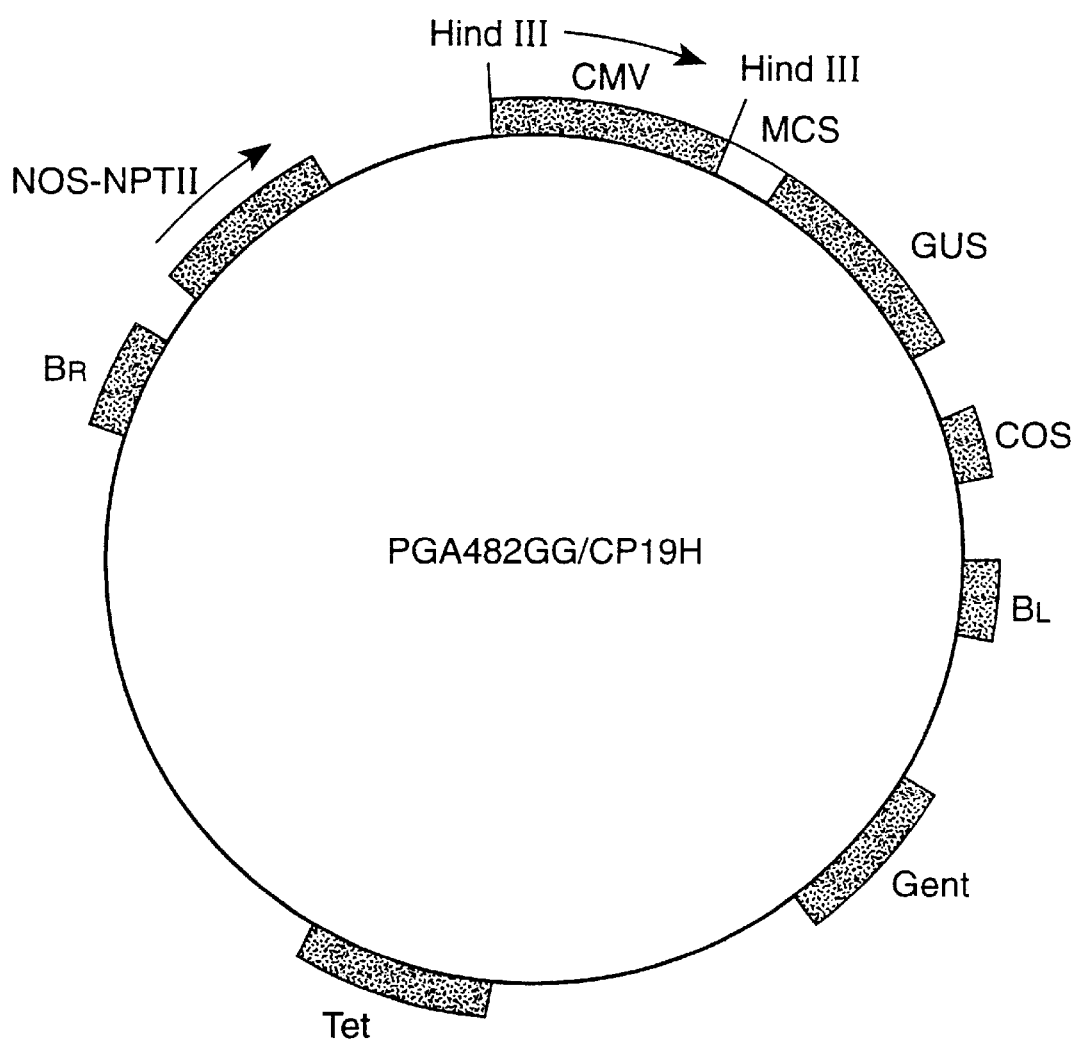

United States Patent [19]
Tricoli et al.

[11] Patent Number: 6,015,942
[45] Date of Patent: Jan. 18, 2000

[54] TRANSGENIC PLANTS EXHIBITING HETEROLOGOUS VIRUS RESISTANCE

[75] Inventors: David M Tricoli; Kim J. Carney, both of Davis, Calif.; Paul F. Russell, Portage, Mich.

[73] Assignee: Seminis Vegetable Seeds, Inc., Saticoy, Calif.

[21] Appl. No.: 08/860,543

[22] PCT Filed: Jun. 7, 1995

[86] PCT No.: PCT/US95/06263

§ 371 Date: Oct. 6, 1997

§ 102(e) Date: Oct. 6, 1997

[87] PCT Pub. No.: WO96/21032

PCT Pub. Date: Jul. 11, 1996

Related U.S. Application Data

[63] Continuation-in-part of application No. 08/367,016, Dec. 30, 1994, abandoned.

[51] Int. Cl.[7] .............................. C12N 5/04; C12N 15/33; C12N 15/82; A01H 1/00
[52] U.S. Cl. .......................... 800/280; 435/419; 435/468; 800/301; 800/308
[58] Field of Search .................................... 800/205, 278, 800/279, 280, 288, 295, 298, 301, 308; 435/172.3, 320.1, 69.1, 410, 419, 468; 536/23.72

[56] References Cited

U.S. PATENT DOCUMENTS

| | | | |
|---|---|---|---|
| 4,940,838 | 7/1990 | Schilperoort et al. | 800/278 |
| 5,258,300 | 11/1993 | Glassman et al. | 800/278 |

FOREIGN PATENT DOCUMENTS

WO 91/10725   7/1991   WIPO .

OTHER PUBLICATIONS

An, *Plant Physiol.*, 81, 86 (1986).
Anderson et al., *Phytopathology*, 79, 1284 (1989).
Bevan et al., *Nucleic Acids Res.*, 11, 369 (1983).
Clark et al., *J. Gen Virol.*, 34, 475 (1977).
Clark et al., *J. Gen Virol.*, 34, 475 (1979).
Crossway et al., *Mol. Gen. Genet.*, 202, 179 (1985).
Depicker et al., *J. Mol. Appl. Genet.*, 1, 561 (1982).
Fromm et al., *Proc. Natl. Acad. Sci. USA*, 82, 824 (1985).
Glover, *DNA Cloning vol. II*, (1985).
Gordon et al., *Virol.*, 123, 284 (1983).
Gould et al., *Eur. J. Biochem.*, 126, 217 (1982).
Herrera–Estrella, *Nature*, 303, 209 (1983).
Jorgensen, Deystone Symposium *Improved Crop and Plant Products through Biotechnology*, Abstract X1–022 (1994).
Klein et al., *Nature*, 327, 70 (1987).
Namba et al., *Gene*, 107, 181 (1991).
Namba et al., *Phytopathology*, 82, 940 (1992).
Paszowski et al., *EMBO J.*, 3, 2717 (1984).
Peden et al., *Virol.*, 53, 487 (1973).
Polites et al., *Biotechniques*, 4, 514 (1987).
Quemada et al., *J. Gen. Virol.*, 53, 487 (1973).
Razaian et al., *Eur. J. Biochem.*, 130, 331 (1985).
Slightom, *Gene*, 100, 251 (1991).
Smith et al., *Nature*, 334, 724 (1988).
Van der Krol et al., *Nature*, 333: 866–869 (1988).
Wu, *Methods of Enzymology*, 68 (1979).
Zaitlin et al., *Virol.*, 201, 200 (1994).
White et al. Virus–induced resistance responses in plants. Critical Review in Plant Sciences. 9(6):443–455, 1991.
A.J. Maule. Virus Movement in infected plants. Critical Review in Plant Sciences. 9(6):457–473, 1991.
Anderson et al. Transgenic plants that express the coat protein genes of tobacco mosaic virus or alfalfa mosaic virus interfere with disease development of some nonrelated viruses. Phytopathology. 79(11):1284–1290, 1989.
Quemada et al. Expression of coat protein gene from cucumber mosaic virus strain C in tobacco: protection against infections by CMV strains transmitted mechanistically or by aphids. Molecular Plant Pathology. 81(7):794–802, 1991.
Namba et al. Protection of transgenic plants expressing the coat protein gene of watermelon mosaic virus II or zucchini yellow mosaic virus against six potyviruses. Phytopathology. 82(9):940–946, 1992.
Choi et al. Genetic transformation and plant regeneration of watermelon using Agrobacterium tumefaciens. Plant Cell Reports. 13:344–348, 1994.
Gonsalves et al., Comparison Of Coat Protein–Mediated And Genetically–Derived Resistance In Cucumbers To Infection By Cucumber Mosaic Virus Under Field Conditions With natural Challenge Inoculations By Vectors, Biotechnology, vol. 10, Dec. 1992.
Lodge et al., Broad–Spectrum Virus Resistance In Transgenic Plants Expressing Pokeweed Antiviral Protein, proc. Natl. Acad. Sci. USA, vol. 90, pp. 7089–7093, Aug. 1993, Genetics.
Beck et al., Disruption Of Virus Movement Confers Broad–Spectrum Resistance Against Systemic Infection By Plant Viruses With A Triple Gene Block, Proc. Natl. Acad. Sci. USA, vol. 91, pp. 10310–10314, Oct. 1994, Plant Biology.
Anderson, Edwin J. et al., Transgenic Plants That Express the Coat Protein Genes of Tobacco Mosaic Virus or Alfalfa Mosaic Virus Interfere with Disease Development of Some Nonrelated Viruses, *Phytopathology*, 79(11):1284–1290, (1989).
Cuzzo, Maria et al., Viral Protection in Transgenic Tobacco Plants Expressing The Cucumber Mosaic Virus Coat Protein or Its Antisense RNA, *Biotechnology* 6:549–557, (1988).
Nejidat, Ali, et al., Engineered Resistance against Plant Virus Diseases, *Physiol. Plant,* 80:662–668, (1990).

*Primary Examiner*—Elizabeth F. McElwain
*Assistant Examiner*—Ashwin D. Mehta
*Attorney, Agent, or Firm*—Rockey, Milnamow & Katz, Ltd.

[57]   ABSTRACT

A method for increasing virus resistance to a transgenic plant comprising a coat protein gene from a cucumber mosaic virus is provided.

8 Claims, 1 Drawing Sheet

TRANSGENIC PLANTS EXHIBITING HETEROLOGOUS VIRUS RESISTANCE

This application is a continuation-in-part of U.S. Ser. No. 08/367,016, filed on Dec. 30, 1994, now abandoned.

FIELD OF THE INVENTION

This invention relates to a coat protein gene derived from cucumber mosaic virus strain C. More specifically, the invention relates to the genetic engineering of plants and to a method for conferring viral resistance to a plant using an expression cassette encoding cucumber mosaic virus strain C coat protein.

BACKGROUND OF THE INVENTION

Many agriculturally important crops are susceptible to infection by plant viruses, particularly cucumber mosaic virus, which can seriously damage a crop, reduce its economic value to the grower, and increase its cost to the consumer. Attempts to control or prevent infection of a crop by a plant virus such as cucumber mosaic virus have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Cucumber mosaic virus (CMV) is a single-stranded (+) RNA plant virus that has a functionally divided genome. The virus genome contains four RNA species designated RNAs 1–4. RNAs 3 and 4 encode the coat protein which is a protein that surrounds the viral RNA and protects the viral RNA from being degraded. Only RNAs 1–3 are required for infectivity because the coat protein, which is encoded by RNA 4, is also encoded by RNA 3.

Several strains of cucumber mosaic virus have been classified using serology, host range, peptide mapping, nucleic acid hybridization, and sequencing analyses. These CMV strains can be divided into two groups, which are designated "WT" (also known as subgroup I) and "S" (also known as subgroup II). The S group consists of at least three members. The WT group is known to contain at least 17 members.

Expression of the coat protein genes from tobacco mosaic virus, alfalfa mosaic virus, cucumber mosaic virus, and potato virus X, among others, in transgenic plants has resulted in plants which are resistant to infection by the respective virus. Heterologous protection can also occur. For example, the expression of coat protein genes from watermelon mosaic virus-2 or zucchini yellow mosaic virus in transgenic tobacco plants has been shown to confer protection against six other potyviruses: bean yellow mosaic virus, potato virus Y, pea mosaic virus, clover yellow vein virus, pepper mottle virus, and tobacco etch virus. However, expression of a preselected coat protein gene does not reliably confer heterologous protection to a plant. For example, transgenic squash plants containing the CMV C coat protein gene, a subgroup I virus, which have been shown to be resistant to the CMV C strain are not protected to the same degree against several highly virulent strains of CMV: CMV V27, CMV V33, and CMV V34 which are all subgroup I viruses.

Thus, a need exists for transgenic plants containing a single viral gene which confers resistance to a plurality of viruses.

SUMMARY OF THE INVENTION

The present invention provides a method of providing heterologous virus resistance to a plant susceptible to infection by two or more viruses by expressing a chimeric recombinant DNA molecule in the cells of the plant which encodes a protein of one class of plant virus, such as a potyvirus protein or cucumovirus protein, i.e., a coat protein or replicase. Unexpectedly, it was found that plants stabely transformed with such recombinant DNA molecules exhibited heterologous virus resistance, in that they were resistant both to infection by the virus from which the encoded protein was derived or isolated, as well as to infection by at least one unrelated class of virus to which the plant is normally susceptible, such as one or more potyviruses. For example, when the known cucumovirus coat protein gene (CMV-C) is expressed in transgenic plants, such as transgenic dicots, it confers protection both against infection by cucumber mosaic virus strains and against infection by zucchini yellow mosaic virus or watermelon mosaic virus-2, i.e., ZYMV and WMV-2. Preferably, the transgenic plant exhibits substantially equal levels of resistance to all of the viruses to which it has become resistant. Although heterologous virus resistance has been demonstrated for closely related viruses, such as potyviruses, it is believed that heterologous virus resistance between unrelated classes of virus has not previously been demonstrated, and the term "heterologous virus resistance" is to be understood in this sense herein below.

Therefore, in a preferred embodiment, the present invention provides a method of imparting multi-virus resistance to a plant which is susceptible to viruses, comprising:

(a) transforming cells of said susceptible plant with a chimeric recombinant DNA molecule comprising a promoter functional in cells of said plant and operably linked to a DNA sequence encoding a protein of a first class of virus which is capable of infecting said plant;

(b) regenerating said plant cells to provide a differentiated plant; and (c) identifying a transformed plant which expresses the coding DNA sequence so as to render the plant resistant to infection by said first class of virus, wherein the plant is also rendered resistant to infection by at least one other class of virus to which said plant is susceptible.

Another embodiment of the present invention provides a method for providing resistance to infection by viruses in a susceptible Cucurbitaceae plant which comprises:

(a) transforming Cucurbitaceae plant cells with a DNA molecule encoding a protein from a first class of virus which is capable of infecting said Cucurbitaceae plant;

(b) regenerating said plant cells to provide a differentiated plant; and (c) selecting a transformed Cucurbitaceae which is expressed so as to render the plant resistant to infection by said first class of said virus, and to at least one other class of said virus.

The present invention is exemplified by the insertion of a virus coat protein (cp) expression cassette into a binary plasmid and subsequent characterization of the resulting plasmid. For example, CMV coat protein expression cassette can be placed in the binary plasmid pPRBN. Subsequently, binary plasmids harboring these expression cassettes are mobilized into Agrobacterium and employed to transfer the virus coat protein genes into plants, such as members of the Cucurbitaceae family, along with the associated selectable marker and/or reporter genes.

As used herein, with respect to a DNA sequence or "gene", the term "isolated" is defined to mean that the sequence is either extracted from its context in the viral genome by chemical means and purified and/or modified to the extent that it can be introduced into the present vectors in the appropriate orientation, i.e., sense or antisense. As used herein, the term "chimeric" is defined to mean the linkage of two or more DNA sequences which are derived from different sources, strains or species, i.e., from bacteria and plants, or that two or more DNA sequences from the same species are linked in a way that does not occur in the native genome. Thus, the DNA sequences useful in the present invention may be naturally-occurring, semi-synthetic or entirely synthetic. The DNA sequence may be linear or circular, i.e, may be located on an intact or linearized plasmid, such as the binary plasmids described below. As used herein, the term "heterologous" is defined to mean not of the same virus class, i.e., a cucomvirus, a potyvirus, a tabovirus, a comovirus, and a geminivirus are all different classes of viruses. As used herein, the term "expression" means transcription or transcription followed by translation of a particular DNA molecule.

BRIEF DESCRIPTION OF THE DRAWINGS

FIG. 1 depicts the binary plasmid pGA482GG/CP19H.

DETAILED DESCRIPTION OF THE INVENTION

Cucumber mosaic virus (CMV) is a single-stranded (+) RNA plant virus that has a functionally divided genome. The virus genome contains four RNA species designated RNAs 1–4; 3389 nucleotides (nt), 3035 nt, 2193 nt, and 1027 nt, respectively (Peden et al., *Virol.,* 53, 487 (1973); Gould et al., *Eur. J. Biochem.,* 126, 217 (1982); Rezaian et al., *Eur. J. Biochem.,* 143, 227 (1984); Rezaian et al., *Eur. J. Biochem.* 150, 331 (1985)). Only RNAs 1–3 are required for infectivity (Peden et al., *Virol.,* 53, 487 (1973)) because the coat protein, which is encoded by RNA 4, is also encoded by RNA 3. Translations of CMV RNAs yield a 95 kD polypeptide from RNA 1, a 94 kD polypeptide from RNA 2 (Gordon et al., *Virol.,* 123, 284 (1983)), and two polypeptides from RNA 3: its 5' end encodes a 35 kD polypeptide, and its 3' end encodes a 24.5 kD polypeptide (Gould et al., *Eur. J. Biochem.,* 126, 217 (1982)). The 24.5 kD polypeptide is identical to that encoded by RNA 4 and is the coat protein.

Several strains of cucumber mosaic virus have been classified using serology, host range, peptide mapping, nucleic acid hybridization, and sequencing. These CMV strains can be divided into two groups, which are designated "WT" (also known as subgroup I) and "S" (also known as subgroup II). CMV subgroup I includes CMV-C, CMV-V27, CMV-V33, CMV-V34, CMV-M, CMV-O, and CMV-Y while subgroup II includes CMV-Q, CMV-WL, and CMV-LS (Zaitlin et al., *Virol.,* 201, 200 (1994)). Protection against a strain in one group does not necessarily provide protection against all strains in that group. For example, transgenic squash plants protected with coat protein genes from the CMV strain C are not protected against the CMV strains V27, V33, or V34. In addition, Zaitlin et al. (*Virol.,* 201, 200 (1994)) report that tobacco plants transgenic for a CMV-FNY replicase gene show protection against challenge from subgroup I strains but show no protection against challenge from subgroup II challenges. Thus, the present invention is directed to providing plants with resistance to CMV-C and at least one other class of virus which can infect said plant.

Another molecular strategy to provide virus resistance in transgenic plants is based on antisense RNA. As is well known, a cell manufactures protein by transcribing the DNA of the gene encoding that protein to produce RNA, which is then processed to messenger RNA (mRNA) (e.g., by the removal of introns) and finally translated by ribosomes into protein. This process may be inhibited in the cell by the presense of antisense RNA. The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature,* 333:866–869 (1988)); or at a more subtle biochemical level, e.g., change in the amount of polygalacturonase and reduction in depolymerization of pectin during tomato fruit ripening (Smith et al., *Nature,* 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology", Abstract X1-022 (1994)). Thus, both antisense and sense RNA have been proven to be useful in achieving downregulation of gene expression in plants.

To practice the present invention, a viral gene must be isolated from the viral genome and inserted into a vector. As used herein, a DNA molecule that encodes a viral coat protein gene includes nucleotides of the coding strand, also referred to as the "sense" strand, as well as nucleotides of the noncoding strand, complementary strand, also referred to as the "antisense" strand, either alone or in their base-paired configuration. Thus, a DNA molecule that encodes the coat protein of CMV-C, for example, includes the DNA molecule having the nucleotide sequence described by Quemada et al., *J. Gen. Virol,* 70, 1065 (1989), a DNA molecule complementary to the nucleotide sequence described by Quemada et al., *J. Gen. Virol,* 70, 1065 (1989)] as well as a DNA molecule which also encodes a CMV coat protein and its complement which hybridizes with a CMV C-specific DNA probe in hybridization buffer with 6×SSC, 5×Denhardt's reagent, 0.5% SDS and 100 μg/ml denatured, fragmented salmon sperm DNA and remains bound when washed at 68° C. in 0.1×SSC and 0.5% SDS (Sambrook et al., *Molecular Cloning: A Laboratory Manual,* 2nd ed. (1989). Moreover, the DNA molecules of the present invention can include non-CMV C coat protein nucleotides that do not interfere with expression of the CMV coat protein gene.

The CMV coat protein gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

When a viral gene expression cassette is placed in a binary plasmid, and that plasmid transformed into a plant, the viral gene preferably exhibits substantially the same degree of efficacy to infection by at least two classes of virus when present in transgenic plants. More preferably, the viral gene preferably exhibits substantially equal efficacy to infection by at least two classes of virus when present in transgenic plants. For example, if one examines numerous transgenic lines containing the viral gene expression cassette, a particular transgenic line will be immune to infection by at least two viruses of different classes to substantially the same degree. Similarly, if a line exhibits a delay in symptom development to one virus, it will also exhibit a delay in symptom development to at least one virus of a different class. Finally, if a line is susceptible to one of the viruses it will be susceptible at least one virus of a different class. Even with single gene constructs, one must test numerous transgenic plant lines to find one that displays the appropriate level of efficacy. The probability of finding a line with useful levels of expression can range from 10–50% (depending on the species involved). For further information refer to Applicants' Assignees copending patent application Ser. No. 08/366,991 entitled "Transgenic Plants Expressing DNA Constructs Containing a Plurality of Genes to Impart Virus Resistance" filed on Dec. 30, 1994 now abandoned, incorporated by reference herein.

Several different methods exist to isolate a viral gene. To do so, one having ordinary skill in the art can use information about the genomic organization of cucumoviruses to locate and isolate the coat protein gene. The coat protein gene is located near the 3' end of RNA 3. Using methods well known in the art, a quantity of virus is grown and harvested. The viral RNA is then separated by gel electrophoresis. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for viral sequences. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library.

CMV coat protein genes from previously isolated strains can be used as hybridization probes to screen the cDNA library to determine if any of the transformed bacteria contain DNA fragments with sequences coding for a CMV coat protein. Alternatively, plasmids which harbor CMV coat protein sequences can be determined by restriction enzyme digestion of plasmids in bacterial transformants. The cDNA inserts in any bacterial colonies which contain this region can be sequenced. The coat protein gene is present in its entirety in colonies which have sequences that extend 5' to the sequence which encodes the ATG start codon and sequences that extend 3' of the stop codon.

Alternatively, cDNA fragments can be inserted in the sense orientation into expression vectors. Antibodies against the coat protein can be used to screen the cDNA expression library and the gene can be isolated from colonies which express the protein.

In the present invention, the DNA molecules encoding the coat protein (CP) gene of the cucumber mosaic virus strain C have been inserted into an expression cassette. This expression cassette can be placed into a vector that can be transmitted into plants, preferably a binary vector. The expression vectors contain the necessary genetic regulatory sequences for expression of an inserted gene. The coat protein gene is inserted such that those regulatory sequences are functional and the genes can be expressed when incorporated into a plant genome.

The segment of DNA referred to as the promoter is responsible for the regulation of the transcription of DNA into mRNA. A number of promoters which function in plant cells are known in the art and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present viral gene expression cassettes include the constitutive promoters from CaMV, the Ti genes nopaline synthase (Bevan et al., *Nucleic Acids Res. II,* 369–385 (1983)) and octopine synthase (Depicker et al., *J. Mol. Appl. Genet.,* 1, 561–564 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or the RNAs effective to provide viral resistance, but not so much as to be detrimental to the cell in which they are expressed. The promoters selected should be capable of functioning in tissues including but not limited to epidermal, vascular, and mesophyll tissues. The actual choice of the promoter is not critical, as long as it has sufficient transcriptional activity to accomplish the expression of the preselected proteins or RNAs, and subsequent conferral of viral resistance to the plants.

The non-translated leader sequence can be derived from any suitable source and can be specifically modified to increase the translation of the mRNA. The 5' non-translated region can be obtained from the promoter selected to express the gene, an unrelated promoter, the native leader sequence of the gene or coding region to be expressed, viral RNAS, suitable eucaryotic genes, or a synthetic gene sequence. The present invention is not limited to the constructs presented in the following examples.

The termination region or 3' non-translated region which is employed is one which will cause the termination of transcription and the addition of polyadenylated ribonucleotides to the 3' end of the transcribed mRNA sequence. The termination region may be native with the promoter region, native with the structural gene, or may be derived from another source, and preferably include a terminator and a sequence coding for polyadenylation. Suitable 3' non-translated regions of the chimeric plant gene include but are not limited to: (1) the 3' transcribed, non-translated regions containing the polyadenylation signal of Agrobacterium tumor-inducing (Ti) plasmid genes, such as the nopaline synthase (NOS) gene, and (2) plant genes like the soybean 7S storage protein genes.

Selectable marker genes may be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like. For example, see Table 1 of PCT WO/91/10725, cited above. The present invention also envisions replacing all of the virus-associated genes with an array of selectable marker genes.

The particular marker employed will be one which will allow for the selection of transformed cells as opposed to those cells which were not transformed. Depending on the number of different host species one or more markers may be employed, where different conditions of selection would be useful to select the different host, and would be known to those of skill in the art. A screenable marker or "reporter gene" such as the β-glucuronidase gene or luciferase gene may be used in place of, or with, a selectable marker. Cells transformed with this gene may be identified by the production of a blue product on treatment with 5-bromo-4-chloro-3-indoyl-β-D-glucuronide (X-Gluc).

In developing the present expression construct, the various components of the expression construct such as the DNA sequences, linkers, or fragments thereof will normally be inserted into a convenient cloning vector, such as a plasmid or phage, which is capable of replication in a bacterial host, such as E. coli. Numerous cloning vectors exist that have been described in the literature. After each cloning, the cloning vector may be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in E. coli cells.

All DNA manipulations are typically carried out in E. coli cells, and the final plasmid bearing the potyvirus expression cassette is moved into Agrobacterium cells by direct DNA transformation, conjugation, and the like. These Agrobacterium cells will contain a second plasmid, also derived from Ti or Ri plasmids. This second plasmid will carry all the vir genes required for transfer of the foreign DNA into plant cells.

Suitable plant transformation cloning vectors include those derived from a Ti plasmid of *Agrobacterium tumefaciens,* as generally disclosed in Glassman et al. (U.S. Pat. No. 5,258,300). In addition to those disclosed, for example, Herrera-Estrella, *Nature,* 303, 209 (1983), Biotechnica (published PCT application PCT WO/91/10725), and U.S. Pat. No. 4,940,838, issued to Schilperoort et al.

A variety of techniques are available for the introduction of the genetic material into or transformation of the plant cell host. However, the particular manner of introduction of the plant vector into the host is not critical to the practice of the present invention, and any method which provides for efficient transformation may be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, transformation using viruses or pollen, chemicals that increase the direct uptake of DNA (Paszkowski et al., *EMBO J.,* 3, 2717 (1984)), microinjection (Crossway et al., *Mol. Gen. Genet.,* 202, 179 (1985)), electroporation (Fromm et al., *Proc. Natl. Acad. Sci.* USA, 82, 824 (1985)), or high-velocity microprojectiles (Klein et al., *Nature,* 327, 70 (1987)).

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present viral gene expression cassette for an effective period of time. This may range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove non-resistant sections. The cells or calli can then be assayed for the presence of the viral gene cassette, or may be subjected to known plant regeneration protocols. In protocols involving the direct production of shoots, those shoots appearing on the selective media are presumed to be transformed and may be excised and rooted, either on selective medium suitable for the production of roots, or by simply dipping the excised shoot in a root-inducing compound and directly planting it in vermiculite.

In order to produce transgenic plants exhibiting multi-viral resistance, a viral gene of the present invention must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral gene present in the transformed vector which are of the same polarity to that of the viral genomic RNA such that they are capable of base pairing with viral specific RNA of the opposite polarity to that of viral genomic RNA under conditions described in Chapter 7 of Sambrook et al. (1989). mRNA molecules also encompassed within the scope of the invention are those which contain viral specific sequences derived from the viral gene present in the transformed vector which are of the opposite polarity to that of the viral genomic RNA such that they are capable of base pairing with viral genomic RNA under conditions described in Chapter 7 of Sambrook et al. (1989).

The presence of a viral gene can also be detected by immunological assays, such as the double-antibody sandwich assays described by Namba et al., *Gene,* 107, 181 (1991) as modified by Clark et al., *J. Gen. Virol.,* 34, 475 (1979). See also, Namba et al., *Phytopathology,* 82, 940 (1992).

Virus resistance can be assayed via infectivity studies as generally disclosed by Namba et al., ibid., wherein plants are scored as symptomatic when any inoculated leaf shows veinclearing, mosaic or necrotic symptoms.

It is understood that the invention is operable when either sense or anti-sense viral specific RNA is transcribed from the expression cassettes described above. That is, there is no specific molecular mechanism attributed to the desired phenotype and/or genotype exhibited by the transgenic plants. Thus, protection against viral challenge can occur by any one or any number of mechanisms.

It is also understood that virus resistance can occur by the expression of any virally encoded gene. For example, a transgenic plant harboring a papaya ringspot virus (PRV) NIa protease gene was found to confer resistance to challenge with PRV (for further information, see Applicants' Assignees copending patent application Ser. No. 08/366,991, entitled "Transgenic Plants Expressing DNA Constructs Containing a Plurality of Genes to Impart Virus Resistance" field on Dec. 30, 1994 now abandoned, incorporated by reference herein). However, transgenic plants harboring a viral gene of one class of plant virus have not been shown to be resistant to challenge by another class of plant virus.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. The farmer typically grows more than one kind of hybrid based on such differences as maturity, disease and insect resistance, color or other agronomic traits. Additionally, hybrids adapted to one part of a country are not adapted to another part because of differences in such traits as maturity, disease and insect tolerance, or public demand for specific varieties in given geographic locations. Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. With respect to transgenic plants of the type disclosed herein, the transgenes exhibit dominant, single gene Mendelian behavior. This genetic analysis can be part of the initial efforts to covert agronomically elite, yet sensitive lines to resistant lines. A conversion process (backcrossing) is carried out by crossing the original resistant line with a sensitive elite line and crossing the progeny back to the sensitive parent. The progeny from this cross will segregate such that some plants carry the resistance gene(s) whereas some do not. Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate back-crossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

The invention will be further described by reference to the following detailed examples. Enzymes were obtained from commercial sources and were used according to the vendor's recommnedations or other variations known in the art. Other reagents, buffers, etc., were obtained from commercial sources, such as Sigma Chemical Co., St. Louis, Mo., unless otherwise specified.

Most of the recombinant DNA methods employed in practicing the present invention are standard procedures, well known to those skilled in the art, and described in detail in, or example, European Patent Application Publication Number 223,452, published Nov. 29, 1986, which is incorporated herein by reference. General references containing such standard techniques include the following: R. Wu, ed. (1979) *Methods in Enzymology*, Vol. 68; J. H. Miller (1972) *Experiments in Molecular Genetics;* J. Sambrook et al. (1989) *Molecular Cloning: A Laboratory Manual* 2nd Ed.; D. M. Glover, ed. (1985) DNA *Cloning Vol. II;* H. G. Polites and K. R. Marotti (1987) "A step-wise protocol for cDNA synthesis," *Biotechniques* 4; 514–520; S. B. Gelvin and R. A. Schilperoort, eds. Introduction, Expression, and Analysis of Gene Products in Plants, all of which are incorporated by reference

EXAMPLE I

Squash Varieties with Multiple Virus Resistance

A. Cucumber Mosaic Virus

The cloning, characterization and engineering of the CMV coat protein gene used in our experiments are described in H. Quemada et al., *J. Gen. Virol.,* 70, 1065 (1989) and Slightom, *Gene,* 100, 251 (1991).

B. Binary Plasmid Vectors

The DNA which was transferred into the plant genomes was contained in binary plasmids (M. Bevan, *Nucleic Acids Res.,* 11, 369 (1983)). The parent binary plasmid was pGA482, constructed by G. An, *Plant Physiol.,* 81, 86 (1986). This vector contains the T-DNA border sequences from pTiT37, the selectable marker gene Nos-NPT II (which contains the plant-expressible nopaline gene promoter fused to the bacterial NPT II gene obtained from Tn5), a multiple cloning region, and the cohesive ends of phage lambda. Insertion of a bacterial gentamycin gene into the SalI site adjacent to the left T-DNA border of pGA482 yielded pGA482GG.

The plant expressible CMV coat protein gene was cloned into the binary plasmid pGA482GG (for further inforamtion, see Applicants' Assignees copending patent application Ser. No. 08/366,991 entitled "Transgenic Plants Expressing DNA Constructs Containing a Plurality of Genes to Impart Virus Resistance" filed on Dec. 30, 1994 now abandoned, incorporated by reference herein) to obtain pGA482GG/ CP19H (FIG. 1). Restriction enzyme site mapping showed that the CMV coat protein gene is oriented in the same direction as the Nos-NPTII gene. Only the region between the two T-DNA border repeats will be transferred into the plant tissues.

C. Squash Transformation

After removal of seed coats, the seeds were surfaced sterilized for 20–25 minutes in a 20% solution of sodium hypochlorite (Clorox) containing tween 20 (200 ul/1000 mls.) Disinfestation was followed by three 100 ml rinses in sterile distilled water. Seeds were germinated in 150×25 mm culture tubes containing 20 mls of ¼ strength Murashige and Skoog minimal organics (MS) medium solidified with 0.8% Difco Bacto Agar. After 5–7 days cotyledons were removed from the seedlings, and shoot tips were excised and transferred to GA7 vessels (Magenta Corp.) containing 75 mls MS medium solidified with 1.5% Difco Bacto Agar. Unless stated otherwise, all cultures were incubated in a growth room at 25° C. with a photoperiod of 16 hours of light. Light was provided with both cool fluorescent (Phillips F40CW) and plant growth (General Electric F40-PF) lamps.

Leaf pieces (0.5 cm) were collected from in vitro plants and soaked in *Agrobacterium tumefaciens* broth culture (OD 600 0.1–0.2) and transferred to 100×20 mm petri dishes containing 40 mls of MS medium supplemented with 1.2 mg/liter 2,4,5-trichlorophenoxyacetic acid (2,4,5-T) and 0.4 mg/liter benzylaminoacid (BAP) (MS-I) with 200 $\mu$M AS. Plates were incubated at 23° C. After two-three days leaf pieces were transferred onto MS-I medium containing 500 mg/liter carbenicillin, 200 mg/liter cefotaxime and 150 mg/liter kanamycin sulfate (MS-IA). After ten days, leaves were transferred to fresh MS-IA medium. Thereafter, tissue was transferred to fresh MIS-IA medium every three weeks. After approximately 16–24 weeks kanamycin resistant embryogenic callus was harvested and transferred to roller tubes containing liquid MS minimal organics medium supplemented with 500 mg/liter carbencillen and 150 mg/liter kanamycin sulfate and 1.03 mg/l $CaCl_2.2H_2O$. Developing embryo ere harvested and transferred to MS minimal organics medium containing 20 mg $AgNO_3$. Germinating embryos were subcultured to fresh medium until rooted shoots were obtained. Plantlets were transferred to soil for $R_1$ seed production.

D. Plant Analysis

Kanamycin resistant transformants were analyzed for the expression of the NPT II gene by ELISA using a commercially available ELISA kit (5-Prime 3-Prime, Boulder, Colo.). Polymerase chain reactions using the appropriate primers were conducted in order to amplify the NPT II gene (adjacent to the right border) and the coat protein gene closest to the left border. Some lines were further characterized using Southern Blot Analysis. Expression of the viral coat protein gene in putatively transformed plants was detected by ELISA utilizing alkaline phosphatase-conjugated antibodies according to the protocol of M. F. Clark et al., *J. Gen. Virol.,* 34, 475 (1977). Antisera to CMV-C, WMV-2, and ZYMV, were provided by D. Gonsalves (Cornell University, Geneva, N.Y.).

The presence or absence of the T-DNA in the $R_1$ and subsequent generations was determined by ELISA tests for the selectable NPT II marker gene. PCR or Southern analysis was used to follow the inheritance in line ZW20 whose advance generations lacked the NPT II gene.

E. Inoculation Procedure

Segregating $R_1$ or $R_2$ progeny along with the appropriate control lines were germinated in the greenhouse. Prior to viral inoculation, cotyledon samples were collected for NPT II ELISA assays. Carborundum dusted cotyledons were mechanically inoculated on six-day-old seedlings with a $1\times10^{-1}$ wt/vol dilution of CMV strain C, ZYMV and WMV-2 which were propagated in *Cucumis sativus, Cucur-* bita pepo and Phaseolus vulgaris, respectively. Plants were inoculated with virus in the greenhouse. Approximately 7–10 days post inoculation, plants were transplanted into the field. In some trials non-inoculated control plants were included in order to monitor some spread of the virus by aphids. Data on symptomatic development were gathered prior to review of the NPT II ELISA results, so the scoring was done without knowledge of the transgenic status of the individual segregant being evaluated.

Plants were given a disease severity rating of 0–9 based on foliage symptoms (0=non-symptomatic, 3=symptoms on inoculated leave and/or very mild symptoms on new growth, 5=moderate systemic spread 7=severe systemic spread, 9=severe systemic spread and stunting). Fruits were also scored according to symptom severity (0=non-symptomatic, 3=mild green blotching of fruit. 5=moderate discoloration. 7=severe discoloration, 9=fruit discoloration and distortion). Each line was then given a disease rating for fruit and foliage which was an average of the individual plant ratings.

F. Field Trial Plot Design

Field trials were carried out under permits issued by Animal and Plant Health Inspection Service (APHIS) of the United States Department of Agriculture (USDA). A design was employed in which each row consisting of a transgenic line was paired with a row containing its non-transgenic counterpart as a control. Each row consisted of 15 plants, two feet apart, with five feet between rows. Two to three replications of each transgenic line were incorporated in each test. Plots were surrounded by a minimum 30 foot border zone of non-transgenic squash plants in order to reduce the flow of transgenic pollen out of the trial site and to monitor for viral spread in the field. Transgenic material incorporated into the test included $R_1$ and $R_2$ progeny from self pollinated or backcrossed $R_0$ yellow crookneck inbred lines. In some cases, a transgenic inbred line was crossed to the appropriate nontransgenic inbred line in order to produce the transgenic versions of the commercial squash hybrids, Pavor or Dixie.

G. Results

As can be seen from the data summarized in Tables 1 and 2, below, all of the transgenic squash line Paro-C-14-40 plants became infected when inoculated with ZYMV or WMV-2. However, as compared to the control plants, the disease ratings for both foliage and fruit were significantly less.

TABLE 1

Heterologous resistance in transgenic squash lines after inoculation with a 1/10 wt/vol dilution of WMV-2.

| LINE | CP | Symptomatic # % | Disease Rating foliage | fruit | Ave # of fruit/ plant |
|---|---|---|---|---|---|
| Pavo-C-14 | + | 13/13 100 | 6.8 | 2.5 | 1.3 |
| CMV-CP gene | – | 15/15 100 | 7.0 | 6.1 | 1.3 |
| Pavo | + | — | — | — | — |
| control | – | 30/30 100 | 7.0 | 7.0 | 1.5 |

TABLE 2

Heterologous resistance in transgenic squash lines after inoculation with a 1/10 wt/vol dilution of ZYMV.

| LINE | CP | Symptomatic # % | Disease Rating foliage | fruit | Ave # of fruit/ plant |
|---|---|---|---|---|---|
| Pavo-C-14-40 | + | 13/13 100 | 6.3 | 6.7 | 1.7 |
| CMV-CP gene | – | 15/15 100 | 6.7 | 8.7 | 1.2 |
| Pavo | + | — | — | — | — |
| control | – | 28/28 100 | 7.2 | 8.7 | 2.2 |

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of increasing virus resistance to a plant which is susceptible to viruses, comprising:

(a) transforming cells of said susceptible plant with a chimeric recombinant DNA molecule comprising a promoter functional in cells of said plant and operably linked to a DNA sequence encoding a coat protein isolated from a cucumber mosaic virus which is capable of infecting said plant;

(b) regenerating said plant cells to provide a differentiated plant; and (c) identifying a transformed plant which expresses said coding DNA coat protein sequence so as to increase the resistance of the plant to infection by said cucumber mosaic virus, wherein the plant further exhibits increased resistance to infection by at least one potyvirus.

2. The method of claim 1 wherein the cucumber mosaic virus is cucumber mosaic virus strain C.

3. The method of claim 1 wherein the potyvirus is watermelon mosaic virus II or zucchini yellow mosaic virus.

4. The method of claim 1 wherein the transformed plant exhibits increased resistance to infection by watermelon mosaic virus II and zucchini yellow mosaic virus.

5. The method of claim 1 wherein the susceptible plant is a dicot.

6. The method of claim 1 wherein the susceptible plant is a member of the Cucurbitaceae family.

7. The method of claim 1 wherein the DNA molecule is part of a binary Ti plasmid and the plant cells are transformed by A. tumefaciens mediated transformation.

8. The method of claim 1 wherein the DNA sequence further comprises a selectable marker gene or a reporter gene that enables identification of said transformed plant.

* * * * *

UNITED STATES PATENT AND TRADEMARK OFFICE
CERTIFICATE OF CORRECTION

PATENT NO.   : 6,015,942
DATED        : January 18, 2000
INVENTOR(S)  : Tricoli et al.

It is certified that error appears in the above-identified patent and that said Letters Patent is hereby corrected as shown below:

<u>Title page,</u>
Item [56], References Cited, OTHER PUBLICATIONS, in the reference "Quemada et al., Expression of coat protein gene from cucumber mosaic virus strain C in tobacco: protection against infections by CMV strains transmitted mechanistically or by aphids", please delete "Molecular Plant Pathology" and insert -- Phytopathology --

Signed and Sealed this

Fifteenth Day of October, 2002

*Attest:*

JAMES E. ROGAN
*Attesting Officer*   *Director of the United States Patent and Trademark Office*